(12) United States Patent
Liu (10) Patent No.: US 9,949,510 B2
(45) Date of Patent: Apr. 24, 2018

(54) ELECTRONIC CIGARETTE

(71) Applicant: KIMREE HI-TECH INC., RoadTown, Tortola (VG)

(72) Inventor: Qiuming Liu, Guangdong (CN)

(73) Assignee: HUIZHOU KIMREE TECHNOLOGY CO., LTD. SHENZHEN BRANCH, Shenzhen, Guangdong (CN)

( * ) Notice: Subject to any disclaimer, the term of this patent is extended or adjusted under 35 U.S.C. 154(b) by 435 days.

(21) Appl. No.: 14/794,081

(22) Filed: Jul. 8, 2015

(65) Prior Publication Data

US 2015/0359265 A1    Dec. 17, 2015

Related U.S. Application Data

(63) Continuation of application No. PCT/CN2014/079936, filed on Jun. 16, 2014.

(51) Int. Cl.
*A24F 1/00* (2006.01)
*A24B 1/00* (2006.01)
(Continued)

(52) U.S. Cl.
CPC .......... *A24F 47/008* (2013.01); *A61M 11/044* (2014.02); *A61M 15/06* (2013.01)

(58) Field of Classification Search
CPC .................................................... A24F 47/008
See application file for complete search history.

(56) References Cited

U.S. PATENT DOCUMENTS

| 8,499,766 | B1 | 8/2013 | Newton | |
|---|---|---|---|---|
| 2011/0011396 | A1* | 1/2011 | Fang | A24F 47/008 128/202.21 |

(Continued)

FOREIGN PATENT DOCUMENTS

| CA | 2641869 A1 | 5/2010 |
|---|---|---|
| CN | 101228969 A | 7/2008 |

(Continued)

OTHER PUBLICATIONS

International Search Report corresponding to Application No. PCT/CN2014/079936; dated Mar. 16, 2015.

*Primary Examiner* — Alex Efta
(74) *Attorney, Agent, or Firm* — U.S. Fairsky LLP; Yue Xu (57) ABSTRACT

An electronic cigarette includes an electronic cigarette body. The electronic cigarette body is provided with an atomizer assembly for atomizing a cigarette liquid; a battery assembly for supplying power to the atomizer assembly; an airflow sensing assembly for sensing a smoking action; and a control module for controlling the battery assembly to supply power to the atomizer assembly. An accommodating space is formed between the atomizer assembly and the battery assembly, and a lamp assembly electrically connected to the battery assembly is accommodated in the accommodating space. A light-transmittable portion for transmitting light emitted from the lamp assembly to the outside of the electronic cigarette body is provided on the sidewall of the electronic cigarette body at a position corresponding to the accommodating space, and a fluorescent layer is provided on the outer surface of the electronic cigarette body at an area corresponding to the light-transmittable portion.

13 Claims, 5 Drawing Sheets

(51) Int. Cl.
      *A24F 1/28*       (2006.01)
      *A24F 1/22*       (2006.01)
      *A24F 47/00*     (2006.01)
      *A61M 11/04*    (2006.01)
      *A61M 15/06*    (2006.01)

(56) References Cited

U.S. PATENT DOCUMENTS

| | | |
|---|---|---|
| 2013/0284194 A1 | 10/2013 | Newton |
| 2014/0182612 A1* | 7/2014 | Chen .................. A24F 47/008 131/329 |
| 2015/0216233 A1* | 8/2015 | Sears .................. A24F 47/008 362/230 |

FOREIGN PATENT DOCUMENTS

| | | | |
|---|---|---|---|
| CN | 202068932 U | * 12/2011 | |
| CN | 103300482 A | 9/2013 | |
| CN | 203194541 U | 9/2013 | |
| CN | 203300709 U | 11/2013 | |
| CN | 203589106 U | 5/2014 | |
| WO | 2014206148 A1 | 12/2014 | |
| WO | WO 2015131991 A1 * | 9/2015 | ........... A24F 47/008 |

* cited by examiner

ELECTRONIC CIGARETTE

CROSS-REFERENCE TO RELATED APPLICATIONS

This application is a continuation of International Application No. PCT/CN2014/079936, filed on Jun. 16, 2014, the entire disclosure of which is incorporated herein by this reference.

TECHNICAL FIELD

The present application relates to the field of electronic products in daily life, and particularly to an electronic cigarette.

BACKGROUND

An electronic cigarette includes an atomizer assembly for atomizing a cigarette liquid and a battery assembly for supplying power to the atomizer assembly. When a user holds an electronic cigarette by the hand, the user usually clamps an area where the atomizer assembly and the battery assembly are connected or an area corresponding to the atomizer assembly, and when the user smokes, an electric heating wire in the area of the atomizer assembly is heated and transfers heat to a casing of the electronic cigarette, thus this area of the casing will be very hot, which may cause discomfort to the user or may even burn the user's finger when the user clamps the area of the atomizer assembly with the finger. Further, as the user is used to smoke the electronic cigarette, the electronic cigarette has been accompanying the user every moment. The electronic cigarette body is usually designed to have a small and short shape to be easy to carry, thus sometimes when the user desires to puff on the electronic cigarette in the night, and it is dark indoor or outdoor, it is inconvenient for the user to locate the electronic cigarette in the night. If a light source is designed in the body of the electronic cigarette to help the user to find the electronic cigarette, the electric power of the battery of the electronic cigarette will be consumed, which may reduce the working duration of the electronic cigarette, and thus it also causes inconvenience to the user.

In addition, the area, where the atomizer assembly and the battery assembly are connected, of the conventional electronic cigarette is generally provided with a key switch for controlling the battery assembly to supply power to the atomizer assembly, a big gap is formed between the key switch and the casing, and the air outside the electronic cigarette is apt to enter into the atomizer assembly through the gap, thus the cigarette liquid in the atomizer assembly is apt to be oxidized by the outside air to become deteriorate. Thirdly, in a conventional electronic cigarette, the cigarette liquid in the atomizer assembly is apt to leak into the battery assembly under the action of capillarity or gravity, and the leaked cigarette liquid may cause short circuit of the battery assembly. Further, the cigarette liquid leaked from the atomizer assembly into the battery assembly may be oxidized, which may generate a abnormal smell in the electronic cigarette, and when the user smokes the electronic cigarette, the user may inhale gas with abnormal smell.

There are disadvantages to be improved in the conventional technology.

SUMMARY

A technical issue to be addressed by the present application is to provide an improved electronic cigarette to solve the disadvantages in the conventional technology.

To address the technical issue, the following technical means are provided in the present application. An electronic cigarette is provided, which includes an electronic cigarette body. The electronic cigarette body is provided with an atomizer assembly configured to atomize a cigarette liquid, a battery assembly configured to supply power to the atomizer assembly, an airflow sensing assembly configured to sense a smoking action, and a control module configured to control the battery assembly to supply power to the atomizer assembly according to a smoking signal transmitted from the airflow sensing assembly. An accommodating space is formed between the atomizer assembly and the battery assembly, the accommodating space is isolated from an area, corresponding to the accommodating space, of an outer peripheral surface of the electronic cigarette body, to allow gas within the accommodating space to be isolated from air outside the outer peripheral surface of the electronic cigarette body at the position corresponding to the accommodating space. A lamp assembly is accommodated in the accommodating space and is electrically connected to the battery assembly, and is configured to emit light when the electronic cigarette is in operation. A light-transmittable portion configured to transmit light emitted from the lamp assembly to the outside of the electronic cigarette body is provided on a sidewall of the electronic cigarette body at a position corresponding to the accommodating space. A fluorescent layer is provided on an outer surface of the electronic cigarette body at an area corresponding to the light-transmittable portion, and is configured to store energy by light exposure and release the energy in the form of visible light in the dark. An intake passage configured to allow airflow to flow in and a smoke passage configured to allow smoke generated by the atomizer assembly to flow out are provided in the electronic cigarette body, the accommodating space is in communication with the intake passage and the smoke passage, to allow the airflow outside the electronic cigarette to flow through the accommodating space after flowing into the intake passage and then flow into the smoke passage.

In the electronic cigarette according to the present application, the light-transmittable portion forms text or pattern for alerting.

In the electronic cigarette according to the present application, the electronic cigarette body further includes an atomizing seat, the atomizer assembly includes a fixed tube fixed on the atomizing seat, a cigarette liquid storing member covering the fixed tube and configured to store the cigarette liquid, and an electric heating wire assembly for atomizing the cigarette liquid, the smoke passage is formed in the fixed tube, and the electric heating wire assembly is provided in the smoke passage and is fixed on the fixed tube.

In the electronic cigarette according to the present application, at least one end of the atomizing seat is accommodated in the accommodating space and located at a position corresponding to the light-transmittable portion, and the atomizing seat is an elastic light guiding member and is configured to guide the light emitted from the lamp assembly to the light-transmittable portion.

In the electronic cigarette according to the present application, the lamp assembly includes a lamp body, a circuit board and a holder, the holder is in a cylindrical shape and is in interference fit with an inner wall of the outer sleeve, an end of the holder abuts against an end of the atomizing seat; the circuit board is retained in the holder and is perpendicular to an axial direction of the holder, and the lamp body is mounted on the circuit board at a side facing the atomizing seat.

In the electronic cigarette according to the present application, the lamp body is an light-emitting diode light.

In the electronic cigarette according to the present application, an indication layer is provided on the outer surface of the electronic cigarette body at the area corresponding to the light-transmittable portion.

In the electronic cigarette according to the present application, the electronic cigarette body further includes an outer sleeve, and the atomizer assembly, the battery assembly, and the lamp assembly are all accommodated within the outer sleeve, and the light-transmittable portion is provided at a corresponding area of the outer sleeve.

The electronic cigarette according to the present application further includes a smoking end in communication with the smoke passage, wherein the smoking end is connected to an end of the outer sleeve away from the battery assembly, and the airflow sensing assembly is provided on an inner side of the outer sleeve at an end away from the atomizing assembly; and the airflow sensing assembly is in communication with the intake passage.

In the electronic cigarette according to the present application, the outer sleeve is a light-transmittable body.

In the electronic cigarette according to the present application, the light-transmittable portion is a light-transmittable hole arranged at the corresponding area of the outer sleeve.

In the electronic cigarette according to the present application, the electronic cigarette body further includes a paster covering an outer sidewall of the outer sleeve, and the indication layer is arranged on the paster at an area corresponding to the light-transmittable portion.

In the electronic cigarette according to the present application, an outer sidewall of the outer sleeve is further provided with a coating layer, and the indication layer is arranged on the coating layer at an area corresponding to the light-transmittable portion.

In the electronic cigarette according to the present application, the outer sleeve includes a battery sleeve and an atomizing sleeve which are detachably connected to each other, the battery assembly is accommodated in the battery sleeve, and the atomizer assembly is accommodated in the atomizing sleeve, an end of the atomizing sleeve close to the battery sleeve is provided with a first electrode connector electrically connected to the atomizer assembly, and an end of the battery sleeve close to the atomizing sleeve is provided with a second electrode connector electrically connected to the battery assembly;

the first electrode connector and the second electrode connector are detachably connected to each other and are electrically connected to each other, the first electrode connector is provided with a first through hole in an axial direction, and the first through hole is in communication with the accommodating space, and the second electrode connector is provided with a second through hole in an axial direction, and the second through hole is in communication with an end of the smoke passage away from the smoking end, and the first through hole is in communication with the second through hole.

In the electronic cigarette according to the present application, the battery assembly includes a battery, and the accommodating space is formed in the battery sleeve and between the battery and the second electrode connector.

In the electronic cigarette according to the present application, the lamp assembly includes a lamp body, a circuit board and a holder, the holder is in a cylindrical shape and is in interference fit with an inner wall of the outer sleeve, an end of the holder abuts against an end of the atomizing seat; the circuit board is retained in the holder and is parallel with an axial direction of the holder, and an end, away from the atomizing seat, of a sidewall of the holder is provided with a light-transmittable hole corresponding to the light-transmittable portion, and the lamp body is arranged on the circuit board and faces the light-transmittable hole.

An electronic cigarette is provided according to the present application, includes an electronic cigarette body. The electronic cigarette body is provided with an atomizer assembly configured to atomize a cigarette liquid, a battery assembly configured to supply power to the atomizer assembly, an airflow sensing assembly configured to sense a smoking action, and a control module configured to control the battery assembly to supply power to the atomizer assembly according to a smoking signal transmitted from the airflow sensing assembly. An accommodating space is formed between the atomizer assembly and the battery assembly, the accommodating space is isolated from an area, corresponding to the accommodating space, of an outer peripheral surface of the electronic cigarette body, to allow gas within the accommodating space to be isolated from air outside the outer peripheral surface of the electronic cigarette body at the position corresponding to the accommodating space. A lamp assembly is accommodated in the accommodating space and is electrically connected to the battery assembly, and is configured to emit light when the electronic cigarette is in operation. A light-transmittable portion configured to transmit light emitted from the lamp assembly to the outside of the electronic cigarette body is provided on a sidewall of the electronic cigarette body at a position corresponding to the accommodating space. A fluorescent layer is provided on an outer surface of the electronic cigarette body at an area corresponding to the light-transmittable portion, and is configured to store energy by light exposure and release the energy in the form of visible light in the dark. An intake passage configured to allow airflow to flow in and a smoke passage configured to allow smoke generated by the atomizer assembly to flow out are provided in the electronic cigarette body, the accommodating space is in communication with the intake passage and the smoke passage, to allow the airflow outside the electronic cigarette to flow through the accommodating space after flowing into the intake passage and then flow into the smoke passage. The electronic cigarette body further includes an atomizing seat, the atomizer assembly includes a fixed tube fixed on the atomizing seat, a cigarette liquid storing member covering the fixed tube and configured to store the cigarette liquid, and an electric heating wire assembly for atomizing the cigarette liquid, the smoke passage is formed in the fixed tube, and the electric heating wire assembly is provided in the smoke passage and is fixed on the fixed tube. At least one end of the atomizing seat is accommodated in the accommodating space and located at a position corresponding to the light-transmittable portion, and the atomizing seat is an elastic light guiding member and is configured to guide the light emitted from the lamp assembly to the light-transmittable portion; and an indication layer is provided on the outer surface of the electronic cigarette body at a position corresponding to the light-transmittable portion. The electronic cigarette further includes a smoking end, the electronic cigarette body further includes an outer sleeve, and the atomizer assembly, the lamp assembly and the battery assembly are all accommodated in the outer sleeve, the smoking end is connected to an end of the outer sleeve away from the battery assembly, and the airflow sensing assembly is arranged at an inner side of the outer sleeve at an end away from the atomizing assembly. The lamp assembly includes a lamp body, a circuit board and a holder, the holder is in a cylindrical shape and is in interference fit with an inner wall of the outer sleeve, an end of the holder abuts against an end of the atomizing seat; the circuit board is retained in the holder and is perpendicular to an axial direction of the holder, and the lamp body is mounted on the circuit board at a side facing the atomizing seat.

The electronic cigarette according to the present application has the following beneficial effects.

By providing the lamp assembly and the light-transmittable portion corresponding to the lamp assembly between the atomizer assembly and the battery assembly, the light can be transmitted to the outside of the electronic cigarette through the light-transmittable portion when the lamp assembly is in operation, to function as an indication, thus a smoker may obtain a clear alert, to avoid using the finger to clamp the electronic cigarette at the area where the atomizer assembly is arranged, thereby solving the problem in the conventional technology that the heat emitted from the atomizer assembly in operation may burn the finger of the user or cause discomfort to the user since the user is accustomed to use the finger to clamp the electronic cigarette at the area where the atomizer assembly is arranged. Further, by providing the fluorescent layer on the outer surface of the electronic cigarette body at the area corresponding to the light-transmittable portion, it is easy to locate the electronic cigarette in the dark, and since the fluorescent layer can continuously obtain energy from the lamp assembly, the problem of the energy being east to run out is solved.

Secondly, since the accommodating space is isolated from the area, corresponding to the accommodating space, of the outer peripheral surface of the electronic cigarette body, and the operation of the electronic cigarette is controlled by the airflow sensing assembly cooperating with the controller, it avoids the problem in the conventional technology that outside air can enter into the atomizer assembly randomly to oxidize the cigarette liquid since the operation of the electronic cigarette is controlled by the key button, and the false trigger of the airflow sensing assembly may also be prevented.

Thirdly, if a high-power lamp assembly is applied during the application, the heat generated by the lamp assembly may also be used to heat the cigarette liquid leaked from the atomizer assembly towards the battery assembly, to avoid the circuit in the battery assembly from being shorted due to the leaked cigarette liquid. Further, the leaked cigarette liquid is dried by the lamp assembly in time, which avoids abnormal smell being generated in the electronic cigarette due to the oxidation of the leaked cigarette liquid, and further avoids the user inhaling gas with abnormal smell. Furthermore, the cigarette liquid is dried by the heat from the lamp assembly, which skillfully avoids the problem that short circuit or electric leakage or the like is apt to occur in the case that a heating element such as an exposed heating plate or heating wire is used for heating, thus the structure of the present application has high reliability and safety, and improves the user experience.

BRIEF DESCRIPTION OF THE DRAWINGS

The present application will be further described in conjunction with embodiments and drawings.

DETAILED DESCRIPTION

Figure 1:
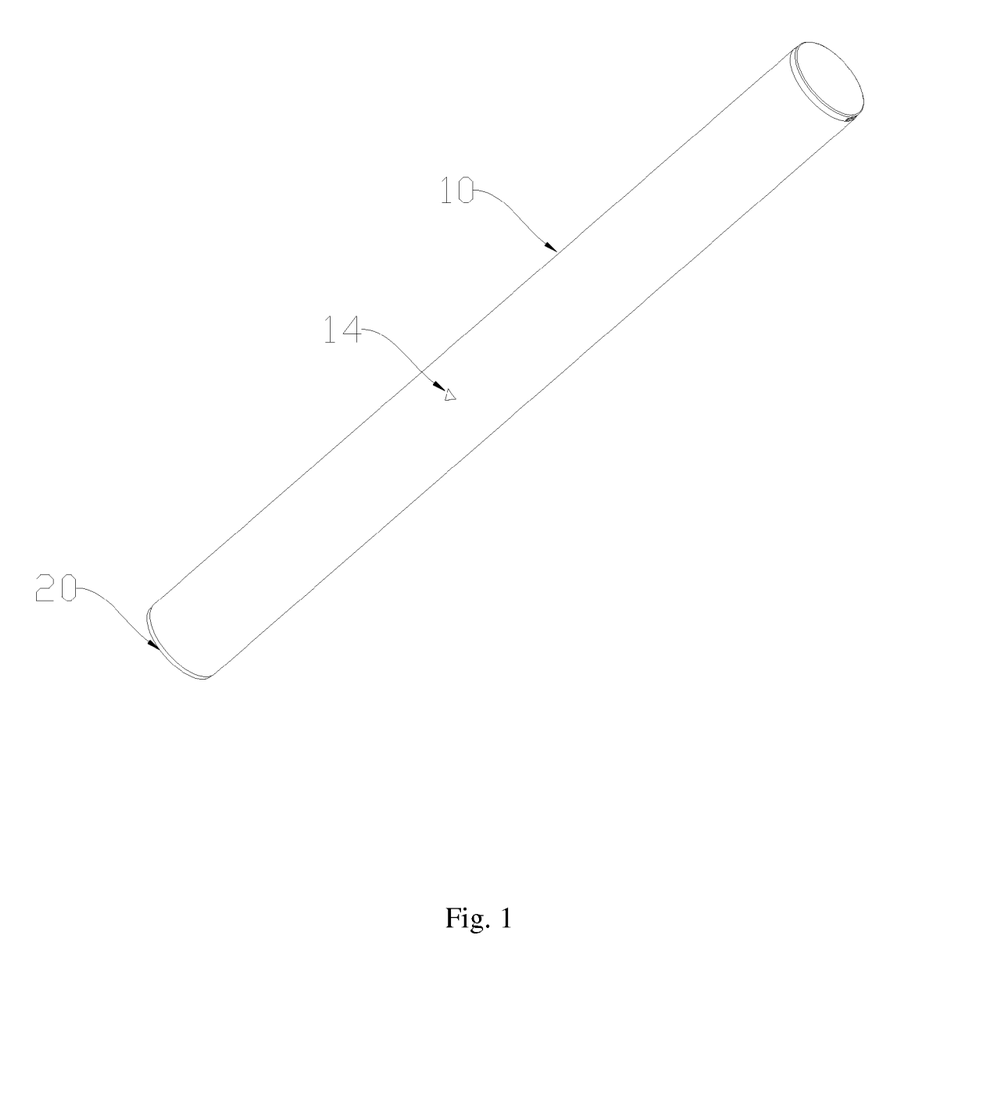
FIG. 1 is a schematic view showing the overall structure of an electronic cigarette according to a first embodiment of the present application.
Figure 2:
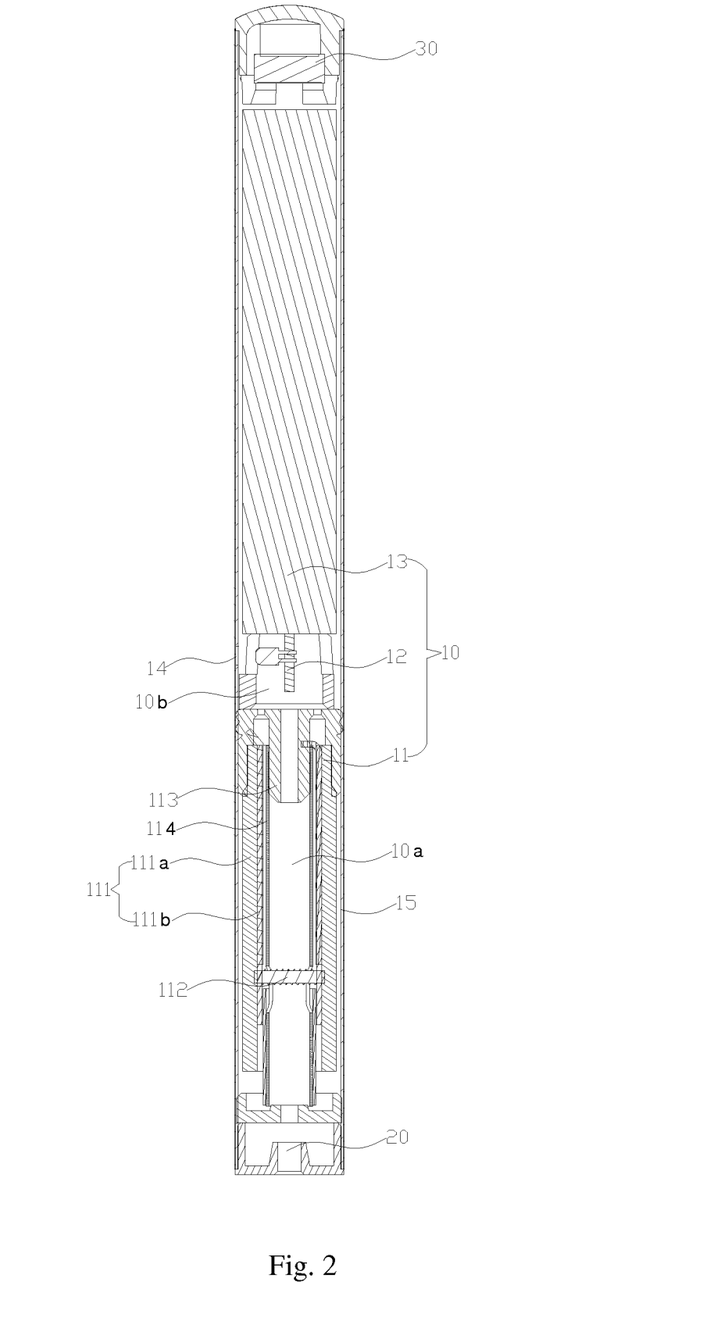
FIG. 2 is a sectional schematic view showing the structure of the electronic cigarette according to the embodiment shown in FIG. 1.

An electronic cigarette according to a first embodiment of the present application is shown in FIG. 1, and reference is also made to FIG. 2, the electronic cigarette includes an electronic cigarette body 10 and a smoking end 20 provided on the electronic cigarette body 10. Specifically, the electronic cigarette body 10 is provided with an atomizer assembly 11 for atomizing a cigarette liquid, a lamp assembly 12, a battery assembly 13 for supplying power to the atomizer assembly 11 and the lamp assembly 12, an airflow sensing assembly 30 for sensing a smoking action, and a control module (not shown) for controlling the battery assembly 13 to supply power to the atomizer assembly 11 according to a smoking signal transmitted from the airflow sensing assembly 30.

An accommodating space 10b is formed between the atomizer assembly 11 and the battery assembly 13, and the accommodating space 10b is isolated from an area, corresponding to the accommodating space 10b, of an outer peripheral surface of the electronic cigarette body. The lamp assembly 12 is accommodated within the accommodating space 10b. A light-transmittable portion 14 for transmitting light emitted from the lamp assembly 12 to the outside of the electronic cigarette body 10 is provided on the sidewall of the electronic cigarette body 10 at a position corresponding to the accommodating space 10b. A fluorescent layer is provided on the outer surface of the electronic cigarette body 10 at an area corresponding to the light-transmittable portion 14, and is capable of storing energy by light exposure and releasing the energy in the form of visible light in the dark. In this embodiment, the smoking end 20 is a suction nozzle cover. Of course, the smoking end 20 may also be an individual suction nozzle or it is not required to provide the suction nozzle, and the structure of the smoking end 20 is not limited here.

By providing the lamp assembly 12 and the light-transmittable portion 14 corresponding to the lamp assembly 12 between the atomizer assembly 11 and the battery assembly 13, the light can be transmitted to the outside of the electronic cigarette through the light-transmittable portion 14 when the lamp assembly 12 is in operation, to function as an indication, thus a smoker may obtain a clear alert, to avoid using the finger to clamp the electronic cigarette at the area where the atomizer assembly 11 is arranged, thereby solving the problem in the conventional technology that the heat emitted from the atomizer assembly 11 in operation may burn the finger of the user or cause discomfort to the user since the user is accustomed to use the finger to clamp the electronic cigarette at the area where the atomizer assembly 11 is arranged. Further, by providing the fluorescent layer on the outer surface of the electronic cigarette body at the area corresponding to the light-transmittable portion, it is easy to locate the electronic cigarette in the dark, and since the fluorescent layer can continuously obtain energy from the lamp assembly, the problem of the energy being east to run out is solved. Secondly, since the accommodating space 10b is isolated from the area, corresponding to the accommodating space 10b, of the outer peripheral surface of the electronic cigarette body, and the operation of the electronic cigarette is controlled by the airflow sensing assembly 30 cooperating with the controller, it avoids the problem in the conventional technology that outside air can enter into the atomizer assembly 11 randomly to oxidize the cigarette liquid since the operation of the electronic cigarette is controlled by the key button, and the false trigger of the airflow sensing assembly may also be prevented. Thirdly, if a high-power lamp assembly 12 is applied during the application, the heat generated by the lamp assembly 12 may also be used to heat the cigarette liquid leaked from the atomizer assembly 11 towards the battery assembly 13, to avoid the circuit in the battery assembly 13 from being shorted due to the leaked cigarette liquid. Further, the leaked cigarette liquid is dried by the lamp assembly 12 in time, which avoids abnormal smell being generated in the electronic cigarette due to the oxidation of the leaked cigarette liquid, and further avoids the user inhaling gas with abnormal smell. Furthermore, the cigarette liquid is dried by the heat from the lamp assembly 12, which skillfully avoids the problem that short circuit or electric leakage or the like is apt to occur in the case that a heating element such as an exposed heating plate or heating wire is used for heating, thus the structure of this embodiment has high reliability and safety, and improves the user experience.

The electronic cigarette body 10 is provided with an intake passage (not shown) for allowing the airflow to flow in and a smoke passage 10a for allowing the smoke generated by the atomizer assembly 11 to flow out. An end of the smoke passage 10a away from the intake passage is in communication with the smoking end 20, and the accommodating space 10b is in communication with the intake passage and another end of the smoke passage 10a. The intake passage may be a gap formed between the battery assembly 13 and an outer sleeve 15, and may also be formed directly in the battery assembly 13, which is not limited here.

When employing this arrangement and using the lamp assembly 12 capable of generating heat, the cold air entered from the intake passage can be preheated in the accommodating space 10b by the heat from the lamp assembly 12, thereby preventing the smoke from being condensed when the smoke runs into the air with too low temperature flowing into the smoke passage 10a. Further, the smoke generated by the lamp assembly 12 heating the cigarette liquid flowing reversely may also be brought into the smoke passage 10a by the airflow flowing through the accommodating space 10b, and thus it may further prevent the cigarette liquid from accumulating in the accommodating space 10b and even flowing into the battery assembly 13.

Specifically, in this embodiment, an indication layer is provided on the outer surface of the electronic cigarette body 10 at an area corresponding to the light-transmittable portion 14, and the fluorescent layer made of a fluorescent material is provided to surround the outer periphery of the indication layer. The fluorescent layer is provided at a position corresponding to the light-transmittable portion 14, and the light-transmittable portion and the indication layer can be made in the form of a text or a pattern, for example, they may be made in the form of a trademark of the electronic cigarette or other patterns, and thus when the lamp assembly 12 emits light, the indication layer is more obvious, and can be easy to be viewed by the user, which improves the user experience. Of course, in other embodiments, the indication layer may be not provided, or the fluorescent layer and the indication layer can be embodied as patterns or texts which are arranged in a manner that one is nested into the other, for example, triangular or circular patterns or text which are arranged in a manner that one is nested into the other. Further, the fluorescent material may be a material available in the market such as zinc sulfide noctilucent powder or rare earth noctilucent powder, and the material is not limited here. The electronic cigarette body 10 also includes an outer sleeve 15, and the atomizer assembly 11, the battery assembly 13, and the lamp assembly 12 are all accommodated within the outer sleeve 15. The smoking end 20 is provided at an end of the outer sleeve 15 away from the battery assembly 13, and of course, may also be provided at an end of the outer sleeve 15 away from atomizer assembly 11. The light-transmittable portion 14 is provided at a corresponding area of the outer sleeve 15.

The outer sleeve 15 may be embodied as a light-transmittable body. An outer sidewall of the outer sleeve 15 is covered with a paster (not shown), and correspondingly, the indication layer is provided at a corresponding area of the paster. Or, the outer peripheral surface of the outer sleeve 15 is coated with a coating layer, which is preferably a paint layer. The coating layer is arranged all over the sidewall surface of the outer sleeve 15, and the indication layer is provided on the coating layer of the outer sleeve 15 at an area corresponding to the light-transmittable portion 14. Other area, except for the area provided with the indication layer, of the coating layer is formed by spraying a light-proof coating or a coating of poor light-transmitting quality. The area of the coating layer corresponding to the indication layer is formed by spraying a light-transmittable coating, and the indication layer may also be formed by spraying a coating at a corresponding area of the coating layer. When the light emitted from the lamp assembly 12 is transmitted to the indication layer through the light-transmittable portion 14, the indication layer is lighted up and can be easily identified by the user. And since the thickness of each of the indication layer and the coating layer is negligible, there is no concave-convex feeling when touching the indication layer and the coating layer, thus the user experience can be improved.

The outer sleeve 15 may also be made of a light-proof material. The light-transmittable portion 14 is a light-transmittable hole arranged in the outer sleeve 15, the outer sidewall of the outer sleeve 15 is covered with a paster (not shown), and correspondingly, the indication layer is provided on the paster at an area corresponding to the light-transmittable portion 14. The light emitted from the lamp assembly 12 is transmitted to the indication layer through the light-transmittable portion 14 to light up the indication layer, thus the indication layer can be easily identified by the user. Specifically, the indication layer is preferably red, other area of the outer surface of the paster is black, thus the indication layer can be much easier identified. Furthermore, the paster can be made of PET (polyethylene glycol terephthalate) or other materials, which is not limited here.

The electronic cigarette body 10 may further include an atomizing seat 113. The atomizer assembly 11 includes a fixed tube 114 fixed on the atomizing seat 113, a cigarette liquid storing member 111 covering the fixed tube 114 and configured to store the cigarette liquid, and an electric heating wire assembly 112 for atomizing the cigarette liquid and fixed on the fixed tube 114. The smoke passage 10a is formed in the fixed tube 114. The atomizing seat 113 is made of an elastic material, to fix the fixed tube 114 and prevent the fixed tube 114 from vibrating, and can also prevent the cigarette liquid from flowing reversely into the accommodating space 10b. The cigarette liquid storing member 111 includes a liquid storage cotton 111a for storing the cigarette liquid and non-woven fabric 111b for guiding the cigarette liquid. The non-woven fabric 111b is covered on the fixed tube 114, and the liquid storage cotton 111a is covered on the non-woven fabric 111b. Of course, the atomizer assembly 11 may also be embodied as other structures, for example, the electric heating wire assembly 112 may be replaced with an ultrasonic atomizing device or the cigarette liquid storing member 111 can be replaced with a liquid cup to store the cigarette liquid, and etc., which is not limited here.

The battery assembly 13 includes a battery and a battery sleeve, the battery assembly 13 may have the structure in the conventional technology as long as it can provide electric energy, and thus the structure is not limited herein. The airflow sensing assembly 30 is accommodated at an inner side of the outer sleeve 15 at an end away from the smoking end 20. When the user smokes the electronic cigarette, the airflow sensing assembly 30 is configured to sense an airflow sucked into the intake passage, and transmit a smoking signal to the control module when it senses the airflow. According to the smoking signal, the control module controls the battery assembly 13 to supply power to the atomizer assembly 11 and the lamp assembly 12. The airflow sensing assembly 30 and the control module are components available in the market, and the structures of which will not be described in detail herein.

Figure 3:
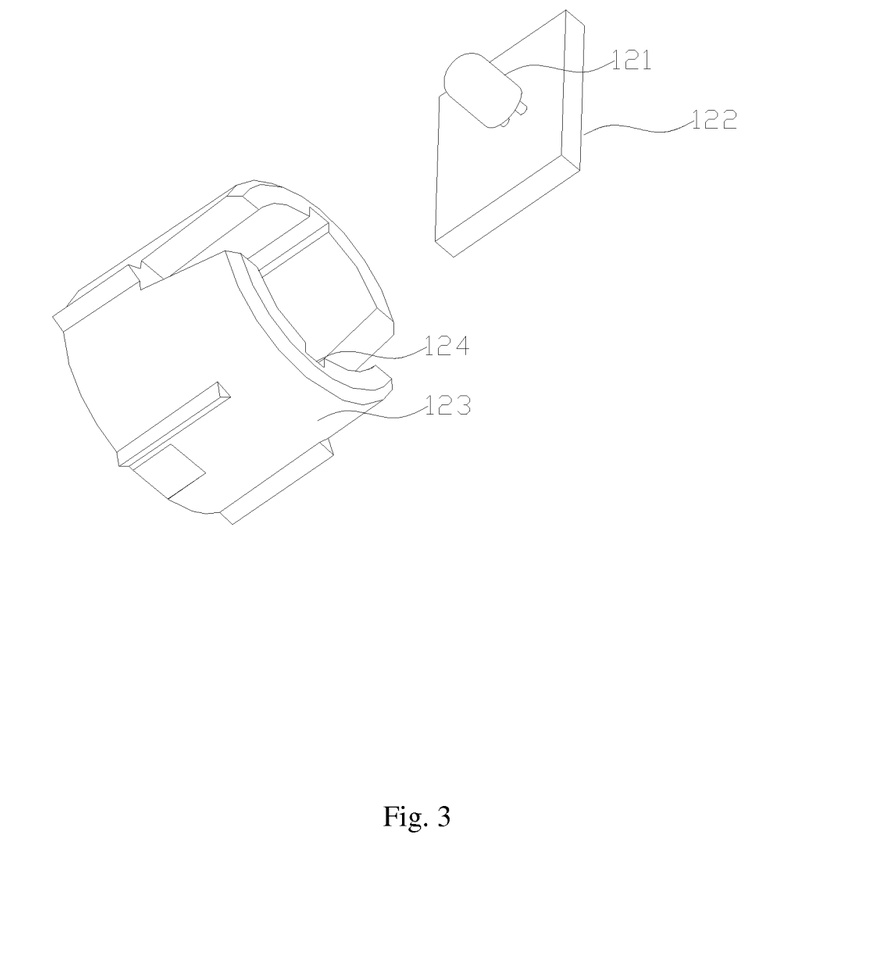
FIG. 3 is an exploded schematic view showing the structure of a lamp assembly according to the embodiment shown in FIG. 1.

Referring to FIG. 3, the lamp assembly 12 includes a lamp body 121, a circuit board 122 and a holder 123. Two retaining grooves 124 are oppositely provided on an inner side of the holder 123, and the lamp body 121 is mounted on the circuit board 122. The circuit board 122 is retained in the two retaining grooves 124, and the holder 123 is retained in the outer sleeve 15 and is located in the accommodating space 10b between the battery of the battery assembly 13 and the atomizer assembly 11. The holder 123 is substantially in a cylindrical shape, and is arranged to be in interference fit with the inner wall of the outer sleeve 15 and is coaxially arranged with the outer sleeve 15. Further, an end of the holder 123 abuts against an end of the atomizing seat 113. An end, away from the atomizing seat 113, of a sidewall of the holder 123 is provided with a light-transmittable opening corresponding to the light-transmittable portion 14. In this embodiment, a board surface of the circuit board 122 is parallel with an axial direction of the holder 123. The lamp body 121 extends in a direction perpendicular to the axial direction of the holder 123 and towards the light-transmittable opening and the light-transmittable portion 14. The lamp body 121 may be composed of one light-emitting diode (LED) light. The light emitted from the LED light is stable and may generate more heat, thus the leaked cigarette liquid may be heated effectively. It can be understood that the lamp body 121 can be embodied as a lamp body which generates more heat. To improve the indication brightness and the amount of heat, the lamp body 121 may include multiple LED lights.

Figure 4:
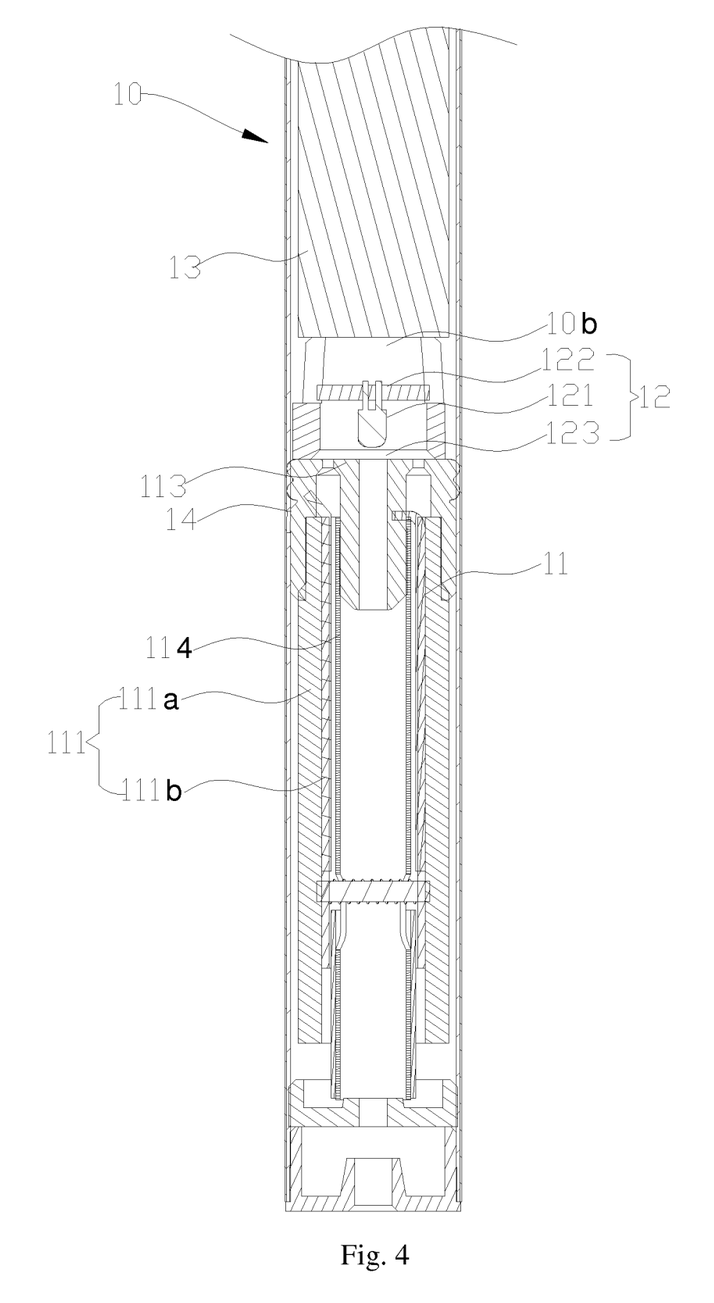
FIG. 4 is a schematic view showing the partial structure of an electronic cigarette according to a second embodiment of the present application.

FIG. 4 shows an electronic cigarette according to a second embodiment of the present application. Unlike the first embodiment, in the electronic cigarette in this embodiment, at least one end of the atomizing seat 113 is accommodated in the accommodating space 10b and located at a position corresponding to the light-transmittable portion 14. An end of the atomizing seat 113 abuts against an end of the holder 123. The circuit board 122 is retained within the holder 123 with the board surface of the circuit board 122 being perpendicular to an axial direction of the atomizing seat 113. The lamp body 121 is mounted on the circuit board 122 at a side facing the atomizing seat 113 and is adjacent to the atomizing seat 113. The atomizing seat 113 is an elastic light guiding member and is configured to guide the light emitted from the lamp assembly 12 to the light-transmittable portion 14. Therefore, the atomizing seat 113 in this embodiment further functions to guide the light. The light emitted from the lamp body 121 is transmitted to the light-transmittable portion 14 by the light guiding function of the atomizing seat 113, and then is transmitted to the indication layer through the light-transmittable portion 14 to light up the indication layer, thereby avoiding a situation that the light at a partial area of the indication layer is too strong to form a light spot, which may influence the user to view the indication layer. In this embodiment, the atomizing seat 113 is made of silica gel, of course, it may also be made of other materials, which is not limited here.

Figure 5:
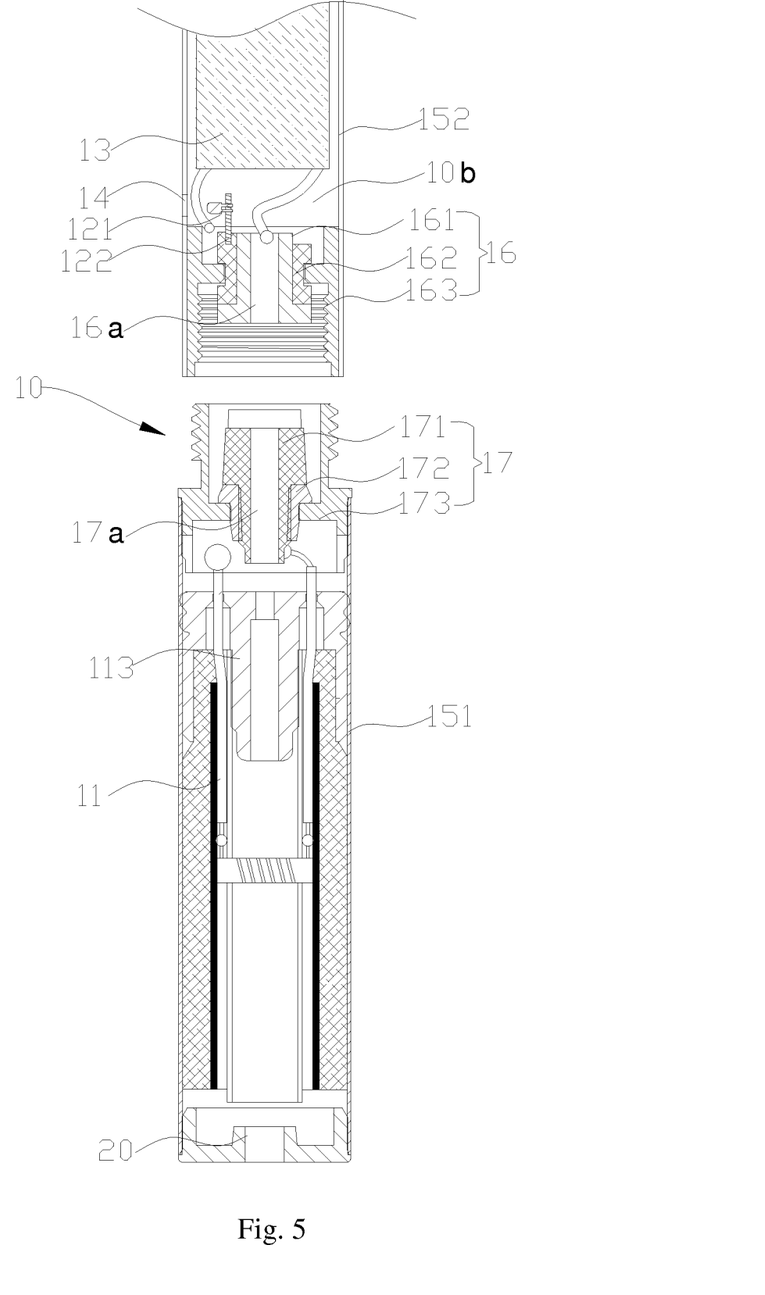
FIG. 5 is a partially exploded schematic view showing the structure of an electronic cigarette according to a third embodiment of the present application.

FIG. 5 shows an electronic cigarette according to a third embodiment of this application. Unlike the first embodiment, in the electronic cigarette in this embodiment, the outer sleeve 15 includes an atomizing sleeve 151 and a battery sleeve 152 which are detachably connected to each other. The battery assembly is accommodated in the battery sleeve 152, and the atomizer assembly 11 is accommodated in the atomizing sleeve 151. The smoking end 20 is connected to an end of the atomizing sleeve 151 away from the battery sleeve 152, and the airflow sensing assembly 30 is arranged at an inner side of the battery sleeve 152 at an end away from the atomizing sleeve 151.

An end of the atomizing sleeve 151 facing the battery sleeve 152 is provided with a first electrode connector 17, and the first electrode connector 17 is electrically connected to the atomizer assembly 11. An end of the battery sleeve 152 facing the atomizing sleeve 151 is provided with a second electrode connector 16, and the second electrode connector 16 is electrically connected to the battery assembly 13. The first electrode connector 17 and the second electrode connector 16 are detachably connected to each other and are electrically connected to each other.

The first electrode connector 17 includes a first inner electrode 171, a first insulating sleeve 172 and a first threaded electrode 173. The first inner electrode 171 is mounted at an inner side of the first threaded electrode 173 and is insulated from the first threaded electrode 173 via the first insulating sleeve 172. The first inner electrode 171 and the first threaded electrode 173 are electrically connected to two terminals of the electrical heating wire assembly 112 of the atomizer assembly 11, respectively.

The second electrode connector 16 includes a second inner electrode 161, a second insulating sleeve 162 and a second threaded electrode 163. The second inner electrode 161 is mounted at an inner side of the second threaded electrode 163 and is insulated from the second threaded electrode 163 via the second insulating sleeve 162. The second inner electrode 161 and the second threaded electrode 163 are electrically connected to two terminals of the battery of the battery assembly 13, respectively.

In this embodiment, the accommodating space 10b is formed between the battery and the second electrode connector 16 inside the outer sleeve 15. Further, the lamp assembly 12 may only include a lamp body 121 and a circuit board 122. The circuit board 122 is inserted in the second insulating sleeve 162 and extends in a direction towards the battery, and the lamp body 121 is disposed perpendicularly on the circuit board 122 and towards the light-transmittable portion 14.

The first inner electrode 171 of the first electrode connector 17 is provided with a first through hole 17a in an axial direction, and the first through hole 17a is in communication with the accommodating space 10b. The second inner electrode 161 of the second electrode connector 16 is provided with a second through hole 16a in an axial direction, and the second through hole 16a is in communication with an end of the smoke passage 10a away from the smoking end 20. The first through hole 17a is in communication with the second through hole 16a.

In the present application, the lamp assembly 12 may function as an indication, to give a smoker a clear alert, to avoid the smoker using the finger to clamp the electronic cigarette at the area where the atomizer assembly 11 is arranged, thereby solving the problem in the conventional technology that the heat emitted from the atomizer assembly 11 in operation may burn the finger of the user since the user is accustomed to use the finger to clamp the electronic cigarette at the area where the atomizer assembly 11 is arranged. Further, when the high-power lamp assembly 12 is in operation, the heat generated by the lamp assembly 12 may heat the cigarette liquid leaked from the atomizer assembly 11 towards the battery assembly 13, thereby avoiding the circuit in the battery assembly 13 from being shorted by the leaked cigarette liquid. Furthermore, the leaked cigarette liquid is dried by the lamp assembly 12 in time, which avoids abnormal smell being generated in the electronic cigarette due to the oxidation of the leaked cigarette liquid, and further avoids the user inhaling gas with abnormal smell.

Since the accommodating space 10b in which the lamp assembly 12 is mounted is in communication with the intake passage and the smoke passage 10a, the cold air entered through the intake passage is preheated in the accommodating space 10b by the heat emitted from the lamp assembly 12, thereby preventing the smoke from being condensed when the smoke runs into the air with too low temperature flowing into the smoke passage 10a. Further, the smoke generated by the lamp assembly 12 heating the cigarette liquid flowing reversely may also be brought into the smoke passage 10a by the airflow flowing through the accommodating space 10b, and thus it may further prevent the cigarette liquid from accumulating in the accommodating space 10b and even flowing into the battery assembly 13.

It should be understood that, for those skilled in the art, the embodiments of the present application are described hereinbefore in conjunction with the drawings, however, the present application is not limited to the specific embodiments described above. The specific embodiments described above are merely illustrative rather than limitation, and with the inspiration of the present application, various forms may also be made by those skilled in the art without departing from the gist of the present application and the scope defined by the claims, for example, the lamp assembly 12 may be embodied as a low-power light source only for supplying light according to requirements, and these forms are all deemed to fall into the scope of the present application.

The invention claimed is:

1. An electronic cigarette, comprising an electronic cigarette body, wherein the electronic cigarette body is provided with an atomizer assembly configured to atomize a cigarette liquid, a battery assembly configured to supply power to the atomizer assembly, an airflow sensing assembly configured to sense a smoking action, and a control module configured to control the battery assembly to supply power to the atomizer assembly according to a smoking signal transmitted from the airflow sensing assembly;

an accommodating space is formed between the atomizer assembly and the battery assembly, the accommodating space is isolated from an area, corresponding to the accommodating space, of an outer peripheral surface of the electronic cigarette body; a lamp assembly is accommodated in the accommodating space and is electrically connected to the battery assembly, and is configured to emit light when the electronic cigarette is in operation; a light-transmittable portion configured to transmit light emitted from the lamp assembly to the outside of the electronic cigarette body is provided on a sidewall of the electronic cigarette body at a position corresponding to the accommodating space, and a fluorescent layer is provided on an outer surface of the electronic cigarette body at an area corresponding to the light-transmittable portion, and is configured to store energy by light exposure and release the energy in the form of visible light in the dark; and an intake passage configured to allow airflow to flow in and a smoke passage configured to allow smoke generated by the atomizer assembly to flow out are provided in the electronic cigarette body, the accommodating space is in fluid communication with the intake passage and the smoke passage, to allow the airflow outside the electronic cigarette to flow through the accommodating space after flowing into the intake passage and then flow into the smoke passage;

wherein, the electronic cigarette body further comprises an outer sleeve, and the atomizer assembly, the battery assembly, and the lamp assembly are all accommodated within the outer sleeve, and the light-transmittable portion is provided at a corresponding area of the outer sleeve;

wherein the electronic cigarette body further comprises an atomizing seat, the atomizer assembly comprises a fixed tube fixed on the atomizing seat, a cigarette liquid storing member covering the fixed tube and configured to store the cigarette liquid, and an electric heating wire assembly for atomizing the cigarette liquid, the smoke passage is formed in the fixed tube, and the electric heating wire assembly is provided in the smoke passage and is fixed on the fixed tube;

wherein at least one end of the atomizing seat is accommodated in the accommodating space and located at a position corresponding to the light-transmittable portion, and the atomizing seat is an elastic light guiding member and is configured to guide the light emitted from the lamp assembly to the light-transmittable portion; and wherein the lamp assembly comprises a lamp body, a circuit board and a holder, the holder is in a cylindrical shape and is in interference fit with an inner wall of the outer sleeve, an end of the holder abuts against an end of the atomizing seat the circuit board is retained in the holder and is perpendicular to an axial direction of the holder, and the lamp body is mounted on the circuit board at a side facing the atomizing seat.

2. The electronic cigarette according to claim 1, wherein the light-transmittable portion forms text or pattern for alerting.

3. The electronic cigarette according to claim 1, wherein the lamp body is a light-emitting diode light.

4. The electronic cigarette according to claim 3, wherein an indication layer is provided on the outer surface of the electronic cigarette body at the area corresponding to the light-transmittable portion.

5. The electronic cigarette according to claim 1, further comprising a smoking end in communication with the smoke passage, wherein the smoking end is connected to an end of the outer sleeve away from the battery assembly, and the airflow sensing assembly is provided on an inner side of the outer sleeve at an end away from the atomizing assembly; and the airflow sensing assembly is in communication with the intake passage.

6. The electronic cigarette according to claim 5, wherein the outer sleeve is a light-transmittable body.

7. The electronic cigarette according to claim 5, wherein the light-transmittable portion is a light-transmittable hole arranged at the corresponding area of the outer sleeve.

8. The electronic cigarette according to claim 5, wherein the electronic cigarette body further comprises a paster covering an outer sidewall of the outer sleeve, and the indication layer is arranged on the paster at an area corresponding to the light-transmittable portion.

9. The electronic cigarette according to claim 5, wherein an outer sidewall of the outer sleeve is further provided with a coating layer, and the indication layer is arranged on the coating layer at an area corresponding to the light-transmittable portion.

10. The electronic cigarette according to claim 1, wherein the outer sleeve comprises a battery sleeve and an atomizing sleeve which are detachably connected to each other, the battery assembly is accommodated in the battery sleeve, and the atomizer assembly is accommodated in the atomizing sleeve, an end of the atomizing sleeve close to the battery sleeve is provided with a first electrode connector electrically connected to the atomizer assembly, and an end of the battery sleeve close to the atomizing sleeve is provided with a second electrode connector electrically connected to the battery assembly; and the first electrode connector and the second electrode connector are detachably connected to each other and are electrically connected to each other, the first electrode connector is provided with a first through hole in an axial direction, and the first through hole is in communication with the accommodating space, and the second electrode connector is provided with a second through hole in an axial direction, and the second through hole is in communication with an end of the smoke passage away from the smoking end, and the first through hole is in communication with the second through hole.

11. The electronic cigarette according to claim 10, wherein the battery assembly comprises a battery, and the accommodating space is formed in the battery sleeve and between the battery and the second electrode connector.

12. An electronic cigarette, comprising an electronic cigarette body, wherein the electronic cigarette body is provided with an atomizer assembly configured to atomize a cigarette liquid, a battery assembly configured to supply power to the atomizer assembly, an airflow sensing assembly configured to sense a smoking action, and a control module configured to control the battery assembly to supply power to the atomizer assembly according to a smoking signal transmitted from the airflow sensing assembly;

an accommodating space is formed between the atomizer assembly and the battery assembly, the accommodating space is isolated from an area, corresponding to the accommodating space, of an outer peripheral surface of the electronic cigarette body; a lamp assembly is accommodated in the accommodating space and is electrically connected to the battery assembly, and is configured to emit light when the electronic cigarette is in operation; a light-transmittable portion configured to transmit light emitted from the lamp assembly to the outside of the electronic cigarette body is provided on a sidewall of the electronic cigarette body at a position corresponding to the accommodating space, and a fluorescent layer is provided on an outer surface of the electronic cigarette body at an area corresponding to the light-transmittable portion, and is configured to store energy by light exposure and release the energy in the form of visible light in the dark; and an intake passage configured to allow airflow to flow in and a smoke passage configured to allow smoke generated by the atomizer assembly to flow out are provided in the electronic cigarette body, the accommodating space is in fluid communication with the intake passage and the smoke passage, to allow the airflow outside the electronic cigarette to flow through the accommodating space after flowing into the intake passage and then flow into the smoke passage;

wherein the electronic cigarette body further comprises an outer sleeve, and the atomizer assembly, the battery assembly, and the lamp assembly are all accommodated within the outer sleeve, and the light-transmittable portion is provided at a corresponding area of the outer sleeve;

wherein the electronic cigarette body further comprises an atomizing seat, the atomizer assembly comprises a fixed tube fixed on the atomizing seat, a cigarette liquid storing member covering the fixed tube and configured to store the cigarette liquid, and an electric heating wire assembly for atomizing the cigarette liquid, the smoke passage is formed in the fixed tube, and the electric heating wire assembly is provided in the smoke passage and is fixed on the fixed tube; and wherein the lamp assembly comprises a lamp body, a circuit board and a holder, the holder is in a cylindrical shape and is in interference fit with an inner wall of the outer sleeve, an end of the holder abuts against an end of the atomizing seat; the circuit board is retained in the holder and is parallel with an axial direction of the holder, and an end, away from the atomizing seat, of a sidewall of the holder is provided with a light-transmittable hole corresponding to the light-transmittable portion, and the lamp body is arranged on the circuit board and faces the light-transmittable hole.

13. An electronic cigarette, comprising an electronic cigarette body, wherein the electronic cigarette body is provided with an atomizer assembly configured to atomize a cigarette liquid, a battery assembly configured to supply power to the atomizer assembly, an airflow sensing assembly configured to sense a smoking action, and a control module configured to control the battery assembly to supply power to the atomizer assembly according to a smoking signal transmitted from the airflow sensing assembly;

an accommodating space is formed between the atomizer assembly and the battery assembly, the accommodating space is isolated from an area, corresponding to the accommodating space, of an outer peripheral surface of the electronic cigarette body; a lamp assembly is accommodated in the accommodating space and is electrically connected to the battery assembly, and is configured to emit light when the electronic cigarette is in operation; a light-transmittable portion configured to transmit light emitted from the lamp assembly to the outside of the electronic cigarette body is provided on a sidewall of the electronic cigarette body at a position corresponding to the accommodating space, and a fluorescent layer is provided on an outer surface of the electronic cigarette body at an area corresponding to the light-transmittable portion, and is configured to store energy by light exposure and release the energy in the form of visible light in the dark;

an intake passage configured to allow airflow to flow in and a smoke passage configured to allow smoke generated by the atomizer assembly to flow out are provided in the electronic cigarette body, the accommodating space is in fluid communication with the intake passage and the smoke passage, to allow the airflow outside the electronic cigarette to flow through the accommodating space after flowing into the intake passage and then flow into the smoke passage;

the electronic cigarette body further comprises an atomizing seat, the atomizer assembly comprises a fixed tube fixed on the atomizing seat, a cigarette liquid storing member covering the fixed tube and configured to store the cigarette liquid, and an electric heating wire assembly for atomizing the cigarette liquid, the smoke passage is formed in the fixed tube, and the electric heating wire assembly is provided in the smoke passage and is fixed on the fixed tube;

at least one end of the atomizing seat is accommodated in the accommodating space and located at a position corresponding to the light-transmittable portion, and the atomizing seat is an elastic light guiding member and is configured to guide the light emitted from the lamp assembly to the light-transmittable portion; and an indication layer is provided on the outer surface of the electronic cigarette body at a position corresponding to the light-transmittable portion;

the electronic cigarette further comprises a smoking end, the electronic cigarette body further comprises an outer sleeve, and the atomizer assembly, the lamp assembly, and the battery assembly are all accommodated in the outer sleeve, the smoking end is connected to an end of the outer sleeve away from the battery assembly, and the airflow sensing assembly is arranged at an inner side of the outer sleeve at an end away from the atomizing assembly; and the lamp assembly comprises a lamp body, a circuit board and a holder, the holder is in a cylindrical shape and is in interference fit with an inner wall of the outer sleeve, an end of the holder abuts against an end of the atomizing seat; the circuit board is retained in the holder and is perpendicular to an axial direction of the holder, and the lamp body is mounted on the circuit board at a side facing the atomizing seat.

* * * * *